United States Patent
Lachenbruch

(10) Patent No.: US 10,765,577 B2
(45) Date of Patent: Sep. 8, 2020

(54) MICROCLIMATE SYSTEM FOR A PATIENT SUPPORT APPARATUS

(71) Applicant: Hill-Rom Services, Inc., Batesville, IN (US)

(72) Inventor: Charles A Lachenbruch, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 633 days.

(21) Appl. No.: 15/194,876

(22) Filed: Jun. 28, 2016

(65) Prior Publication Data

US 2017/0000671 A1 Jan. 5, 2017

Related U.S. Application Data

(60) Provisional application No. 62/186,410, filed on Jun. 30, 2015.

(51) Int. Cl.
*A61G 7/057* (2006.01)
*G16H 40/63* (2018.01)
*A61G 7/00* (2006.01)

(52) U.S. Cl.
CPC ...... *A61G 7/05792* (2016.11); *A61G 7/05784* (2016.11); *G16H 40/63* (2018.01); *A61G 7/001* (2013.01); *A61G 2203/16* (2013.01); *A61G 2203/40* (2013.01); *A61G 2203/70* (2013.01)

(58) Field of Classification Search
CPC ............ A61G 2203/16; A61G 2203/30; A61G 2203/34; A61G 2203/36; A61G 2203/40; A61G 2203/46; A61G 2203/70; A61G 7/001; A61G 7/015; A61G 7/018; A61G 7/0507; A61G 7/0513; A61G 7/057; A61G 7/0573; A61G 7/05769; A61G 7/05776; A61G 7/05784; A61G 7/05792; G06F 19/00; G16H 40/63

See application file for complete search history.

(56) References Cited

U.S. PATENT DOCUMENTS

| 4,947,500 | A |   | 8/1990 | Seiler |
| 4,989,283 | A |   | 2/1991 | Krouskop et al. |
| 5,170,364 | A |   | 12/1992 | Gross et al. |
| 5,283,735 | A |   | 2/1994 | Gross et al. |
| 5,560,374 | A | * | 10/1996 | Viard ................ A61G 7/05769 5/713 |
| 5,815,864 | A |   | 10/1998 | Sloop |
| 6,034,526 | A |   | 3/2000 | Montant et al. |
| 6,079,068 | A |   | 6/2000 | Viard et al. |

(Continued)

OTHER PUBLICATIONS

European Search Report from EP 16 17 6845, dated Nov. 16, 2017, 9 pages.

*Primary Examiner* — Nicholas F Polito
(74) *Attorney, Agent, or Firm* — Barnes & Thornburg LLP

(57) ABSTRACT

According to the present disclosure, a microclimate system includes a support surface, an air box, and an immersion sensor. The support surface is configured to support a patient and conduct air along a surface of the support surface so that heat and moisture from a patient lying on the support surface are drawn away from the surface. The air box includes a blower coupled to the support surface to provide airflow to the support surface. The immersion sensor is configured to detect the immersion of the patient into the support surface.

20 Claims, 8 Drawing Sheets

(56) References Cited

U.S. PATENT DOCUMENTS

| | | | |
|---|---|---|---|
| 6,094,762 A | 8/2000 | Viard et al. | |
| 6,145,143 A | 11/2000 | Hicks et al. | |
| 6,223,369 B1 | 5/2001 | Maier et al. | |
| 6,385,803 B1 | 5/2002 | Viard | |
| 6,497,720 B1 | 12/2002 | Augustine et al. | |
| 6,623,080 B2 | 9/2003 | Clapper | |
| 6,699,266 B2 | 3/2004 | Lachenbruch et al. | |
| 6,772,825 B2 | 8/2004 | Lachenbruch et al. | |
| 6,943,694 B1 | 9/2005 | Ellis | |
| 7,273,490 B2 | 9/2007 | Lachenbruch | |
| 7,727,267 B2 | 6/2010 | Lachenbruch | |
| 8,117,701 B2 * | 2/2012 | Bobey | A61G 7/05776 340/815.69 |
| 8,531,307 B2 | 9/2013 | Lachenbruch | |
| 8,578,527 B2 | 11/2013 | Lachenbruch et al. | |
| 8,598,893 B2 | 12/2013 | Camus | |
| 8,745,797 B2 | 6/2014 | Misaki et al. | |
| 8,800,078 B2 | 8/2014 | Lachenbruch et al. | |
| 8,868,244 B2 | 10/2014 | Genaro | |
| 8,959,685 B2 | 2/2015 | Misaki et al. | |
| 9,021,638 B2 | 5/2015 | Misaki | |
| 9,030,331 B2 | 5/2015 | Lachenbruch | |
| 9,138,064 B2 | 9/2015 | Tursi, Jr. et al. | |
| 9,266,455 B2 | 2/2016 | Uramichi et al. | |
| 9,326,903 B2 | 5/2016 | Locke | |
| 9,333,136 B2 | 5/2016 | Gibson et al. | |
| 9,358,138 B2 | 6/2016 | Kelley et al. | |
| 9,392,875 B2 | 7/2016 | Weyl | |
| 9,463,124 B2 | 10/2016 | Lachenbruch et al. | |
| 2003/0030319 A1 | 2/2003 | Clapper | |
| 2003/0046762 A1 | 3/2003 | Stolpmann | |
| 2005/0076715 A1 | 4/2005 | Kuklis et al. | |
| 2009/0217460 A1 | 9/2009 | Bobey et al. | |
| 2009/0282908 A1 | 11/2009 | Homayoun et al. | |
| 2010/0198321 A1 | 8/2010 | Moeck | |
| 2010/0274331 A1 * | 10/2010 | Williamson | A61G 7/05738 607/104 |
| 2010/0308846 A1 | 12/2010 | Camus | |
| 2011/0068939 A1 * | 3/2011 | Lachenbruch | A61B 5/002 340/626 |
| 2011/0185509 A1 | 8/2011 | Genaro | |
| 2011/0218684 A1 | 9/2011 | Genaro | |
| 2012/0277641 A1 | 11/2012 | Wasowski | |
| 2013/0061396 A1 * | 3/2013 | Lafleche | A61G 7/05715 5/600 |
| 2013/0082723 A1 | 4/2013 | Locke | |
| 2013/0104312 A1 | 5/2013 | O'Reagan | |
| 2013/0214583 A1 | 8/2013 | Uramichi et al. | |
| 2013/0263379 A1 | 10/2013 | Misaki et al. | |
| 2014/0013514 A1 | 1/2014 | Misaki | |
| 2014/0059781 A1 | 3/2014 | Lafleche et al. | |
| 2014/0101862 A1 | 4/2014 | Misaki | |
| 2014/0130264 A1 | 5/2014 | Misaki et al. | |
| 2014/0196210 A1 | 7/2014 | Lachenbruch et al. | |
| 2014/0228918 A1 | 8/2014 | Brienza et al. | |
| 2014/0309750 A1 | 10/2014 | Kelley et al. | |
| 2016/0022521 A1 * | 1/2016 | Darnold | A61G 7/05776 700/283 |

* cited by examiner

MICROCLIMATE SYSTEM FOR A PATIENT SUPPORT APPARATUS

CROSS REFERENCE TO RELATED APPLICATIONS

The present application claims the benefit, under 35 U.S.C. § 119(e), of U.S. Provisional Application No. 62/186,410, filed Jun. 30, 2015, which is hereby incorporated by reference herein.

BACKGROUND

The present disclosure is related to microclimate systems, and in particular to microclimate control systems used in patient supports, such as hospital beds. The present disclosure may also be applicable to other types of patient supports, such as recovery beds, wheel chairs, surgical tables and the like.

Microclimate systems are typically used to cool and dry a patient's skin around the interface of the patient's skin with a support surface. Cool and dry skin is helpful to patient health and is less likely to develop decubitus ulcers (bed sores) during stays on a patient support.

Some microclimate systems blow air along the interface of a patient's skin with a support surface. Such systems may be rated to remove a predetermined amount of heat and moisture from a patient's skin when operated. Sometimes, microclimate systems that are rated to remove predetermined amounts of heat and moisture can fail to perform at rated levels due to restricted airflow through the microclimate system from compression of the microclimate system, for example, as a result of supporting the patient.

SUMMARY

The present application discloses one or more of the features recited in the appended claims and/or the following features which, alone or in any combination, may comprise patentable subject matter:

According to the present disclosure, a microclimate system may include a support surface, an air box, and an immersion sensor. The support surface may include a topper. The topper may be configured to conduct air along a top face of the support surface so that heat and moisture from a patient lying on the support surface are drawn away from the top face of the support surface. The air box may include a controller and a blower coupled to the controller and coupled to the topper. The immersion sensor unit may be coupled to the controller. The immersion sensor unit may be configured to detect immersion information corresponding to the immersion of the patient into the support surface. The controller may receive the immersion information from the immersion sensor unit, determine if current operating parameters of the air box provide a rated level of heat withdrawal or evaporative capacity through the topper based at least in part on the immersion information. The controller may update the current operating parameters of the air box if the current operating parameters of the air box do not provide the rated level of heat withdrawal or evaporative capacity through the topper.

In illustrative embodiments, the controller may update the flow rate of the air delivered to the support surface by the air box. In illustrative embodiments, the controller may update the humidity of the air delivered to the support surface by the air box. In illustrative embodiments, the controller may update the temperature of the air delivered to the support surface by the air box. In illustrative embodiments, the controller may update the humidity of the air delivered to the support surface by the air box.

In illustrative embodiments, the controller may update the temperature of the air delivered to the support surface by the air box. In illustrative embodiments, the controller may update the humidity of the air delivered to the support surface by the air box. In illustrative embodiments, the controller may update the humidity of the air delivered to the support surface by the air box.

In illustrative embodiments, the immersion sensor may include an induction sensor including a metal element and an inductive element.

In illustrative embodiments, the inductive element may include an inductive coil spaced apart from and positioned beneath the topper. The metal element may include a metal foil positioned between the topper and the inductive coil. The metal foil may be spaced apart from the inductive coil to form a gap therebetween.

According to another aspect of the present disclosure, a microclimate system may include a topper, an air box, and an immersion sensor. The air box may include a controller and a blower coupled to the controller and coupled to the topper. The immersion sensor unit may be coupled to the controller. The immersion sensor unit may be configured to detect immersion information corresponding to the immersion of the patient into the topper. The controller may receive the immersion information from the immersion sensor unit, determine if current operating parameters of the air box provide a rated level of heat withdrawal or evaporative capacity through the topper based at least in part on the immersion information, and update the current operating parameters of the air box if the current operating parameters of the air box do not provide the rated level of heat withdrawal or evaporative capacity through the topper.

In illustrative embodiments, the controller may update a flow rate of the air delivered to the topper by the air box. In illustrative embodiments, the controller may update a humidity of the air delivered to the topper by the air box.

In illustrative embodiments, the controller may update a temperature of the air delivered to the topper by the air box. In illustrative embodiments, the immersion sensor may include an induction sensor including a metal element and an inductive element.

According to the disclosure, a method of controlling a microclimate system is taught. The microclimate system may include a topper and an air box coupled to the topper to provide pressurized air to the topper. The method may include the steps of receiving information from an immersion sensor corresponding to an immersion of a patient supported on the microclimate system into the topper, determining if current operating parameters of the air box provide a rated level of heat withdrawal or evaporative capacity through the topper based at least in part on the information, and updating the current operating parameters of the air box if the current operating parameters of the air box do not provide the rated level of heat withdrawal or evaporative capacity through the topper.

In illustrative embodiments, determining if the current operating parameters of the air box will provide the rated level of heat withdrawal or evaporative capacity may include (i) looking up an actual level of heat withdrawal or evaporative capacity corresponding to the received information in a first look-up table and (ii) comparing the actual level of heat withdrawal or evaporative capacity parameters with the rated level of heat withdrawal and evaporative capacity. In illustrative embodiments, updating the current operating parameters may include modifying one or more of a flow rate, temperature, and humidity of air moved by the air box.

In illustrative embodiments, the immersion sensor may include an inductive sensor. In illustrative embodiments, the sensor may include a pressure sensor.

Additional features alone or in combination with any other feature(s), including those listed above and those listed in the claims and those described in detail below, can comprise patentable subject matter. Others will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
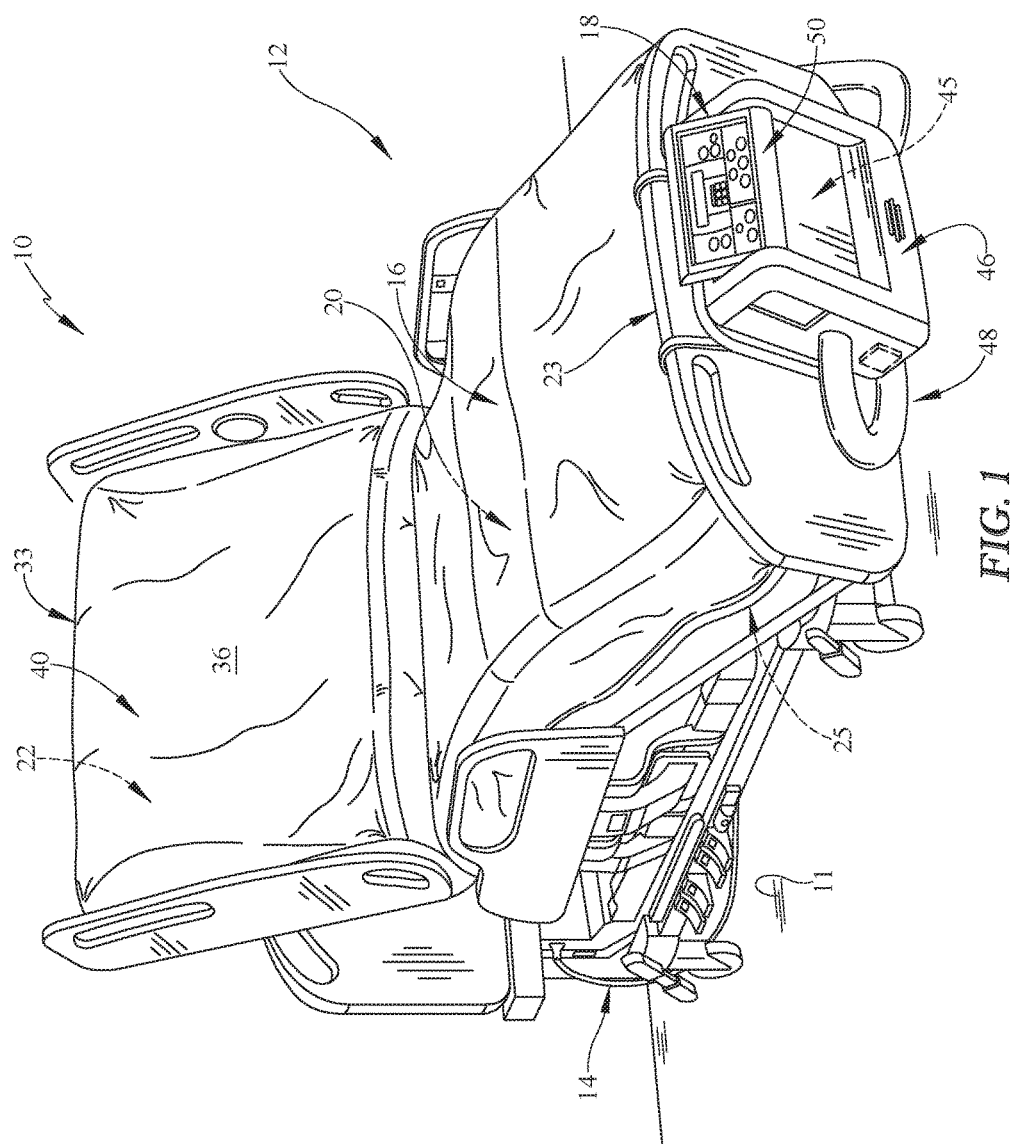
FIG. 1 is perspective view of an illustrative patient support apparatus including a microclimate system supported on a frame structure, the microclimate system includes a support surface, an air box coupled to the support surface, and an immersion sensor operable to measure an immersion of a patient supported on the support surface.

An illustrative patient support apparatus 10 embodied as a hospital bed includes a microclimate system 12 mounted on a frame structure 14 that supports the microclimate system 12 above a floor 11 as shown in FIG. 1. The microclimate system 12 is arranged to underlie a patient supported on the bed 10 and is configured to cool and dry an interface between the patient and the bed 10 to promote skin health by moving air along the interface. The microclimate system 12 is operable to detect compressed portions of the microclimate system 12 that restrict airflow along the interface and degrade performance. The microclimate system 12 is configured to modify one or more of the flow rate, temperature, and humidity of the air moved along the interface to maintain a rated performance in the restricted portions of the microclimate system 12.

Figure 2:
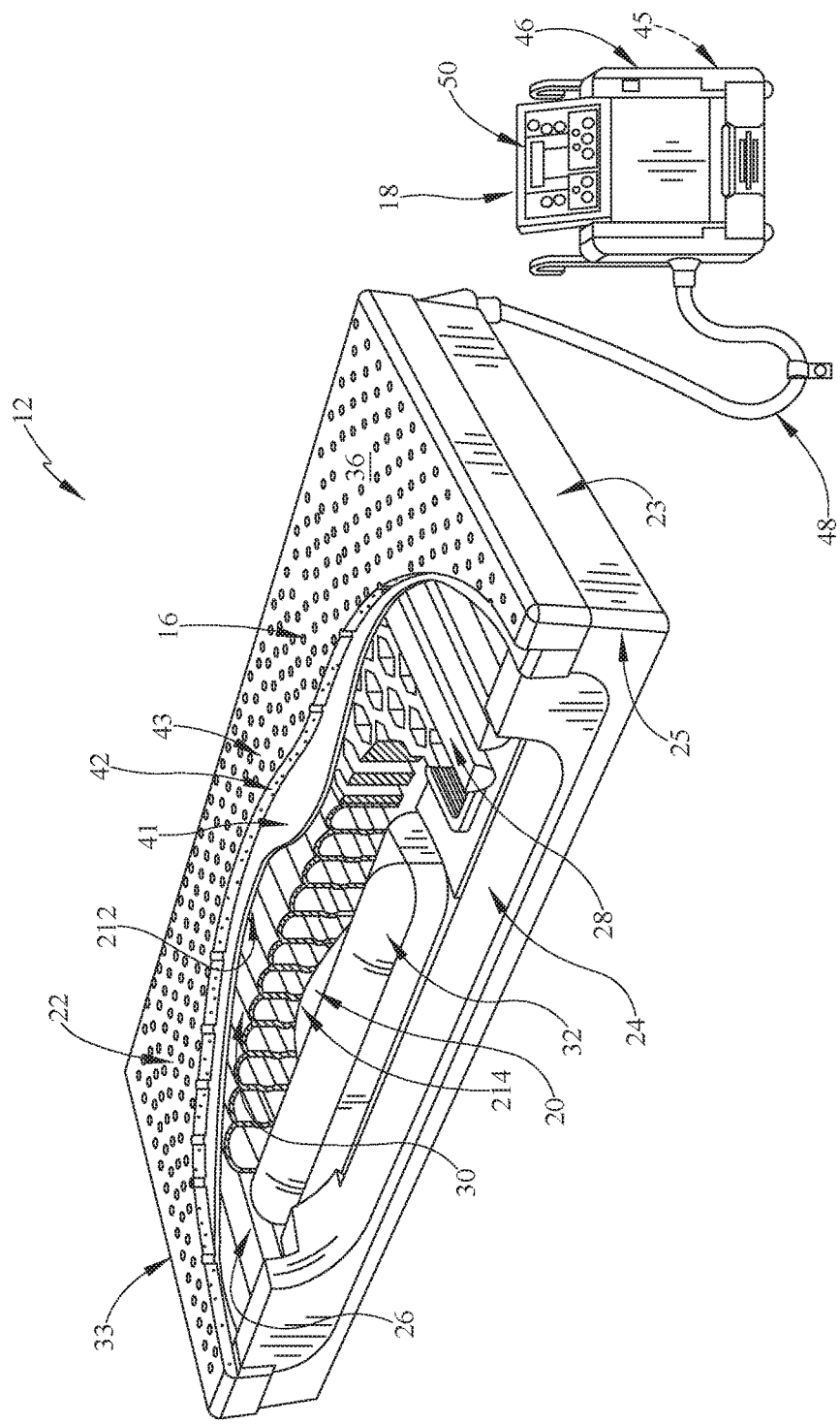
FIG. 2 is a perspective view of the microclimate system of FIG. 1, the support surface includes a topper configured to conduct conditioned air along the interface between a patient and the support surface and body bladders supporting the topper and the immersion sensor is located between the topper and the body bladders and configured to detect compressed portions of the topper with degraded performance properties.

The illustrative microclimate system 12 includes a support surface 16, an air box 18, and an immersion sensor 20 as shown in FIGS. 1 and 2. The support surface 16, sometimes called a mattress, is configured to underlie a patient supported on the bed 10. The air box 18 is coupled to the support surface 16 and is configured to provide conditioned air to the support surface 16 in order to cool and dry the interface between a patient and the support surface 16 when the patient is supported on the bed 10. The immersion sensor 20 is configured to detect compressed portions of the support surface 16 that restrict airflow along the interface. The immersion sensor 20 sends immersion signals indicative of the immersion of a patient into the support surface to the air box 18 and the air box 18 modifies one or more of the flow rate, temperature, and humidity to compensate for the restricted airflow.

Illustratively, the support surface 16 comprises a deformable support surface such as, for example, a mattress. In the illustrative embodiment, the support surface 16 includes a topper 22 and a lower ticking 25 that cooperate to encase a foam shell 24, a foam head section 26, a foam foot section 28, body bladders 30, and turn bladders 32 as shown, for example, in FIG. 3. The topper 22 forms a top face 36 of the support surface 16 and is configured to conduct conditioned air provided by the air box 18 along the interface between a patient and the support surface 16 when the patient is supported on the bed 10. The foam components 24, 26, 28 and the bladders 30, 32 cooperate to support a patient when the patient is supported on the bed 10. In some embodiments, the support surface 16 may also include a coverlet 40 encasing the topper 22 and the lower ticking 25 as shown in FIG. 1.

The topper 22 illustratively includes a bottom layer 41, a middle layer 42, and a top layer 43 as shown in FIG. 2. The middle layer 42 is illustratively a three-dimensional material that allows conditioned air to flow between the bottom layer 41 and the top layer 43 along the top face 36 of the support surface 16 from a foot end 23 to a head end 33 of the support surface 16 as suggested by arrows 44 in FIG. 3. The top layer 43 is made from a perforated material that allows moisture from a patient supported on the topper 22 to pass through the top layer 43 and be carried away for evaporation by conditioned air flowing through the middle layer 42 of the topper 22. In other embodiments, other air-flow cooled toppers may be used with the support surface 16. For example, air-loss toppers, air-fluidized bead toppers, and the like can be used in support surface 16.

The air box 18 is illustratively adapted to be mounted on the frame structure 14, as shown in FIG. 1, but in other embodiments may be integrated into the frame structure 14. The air box 18 is coupled to the support surface 16 to provide air to the support surface 16, as shown in FIG. 2.

Figure 4:
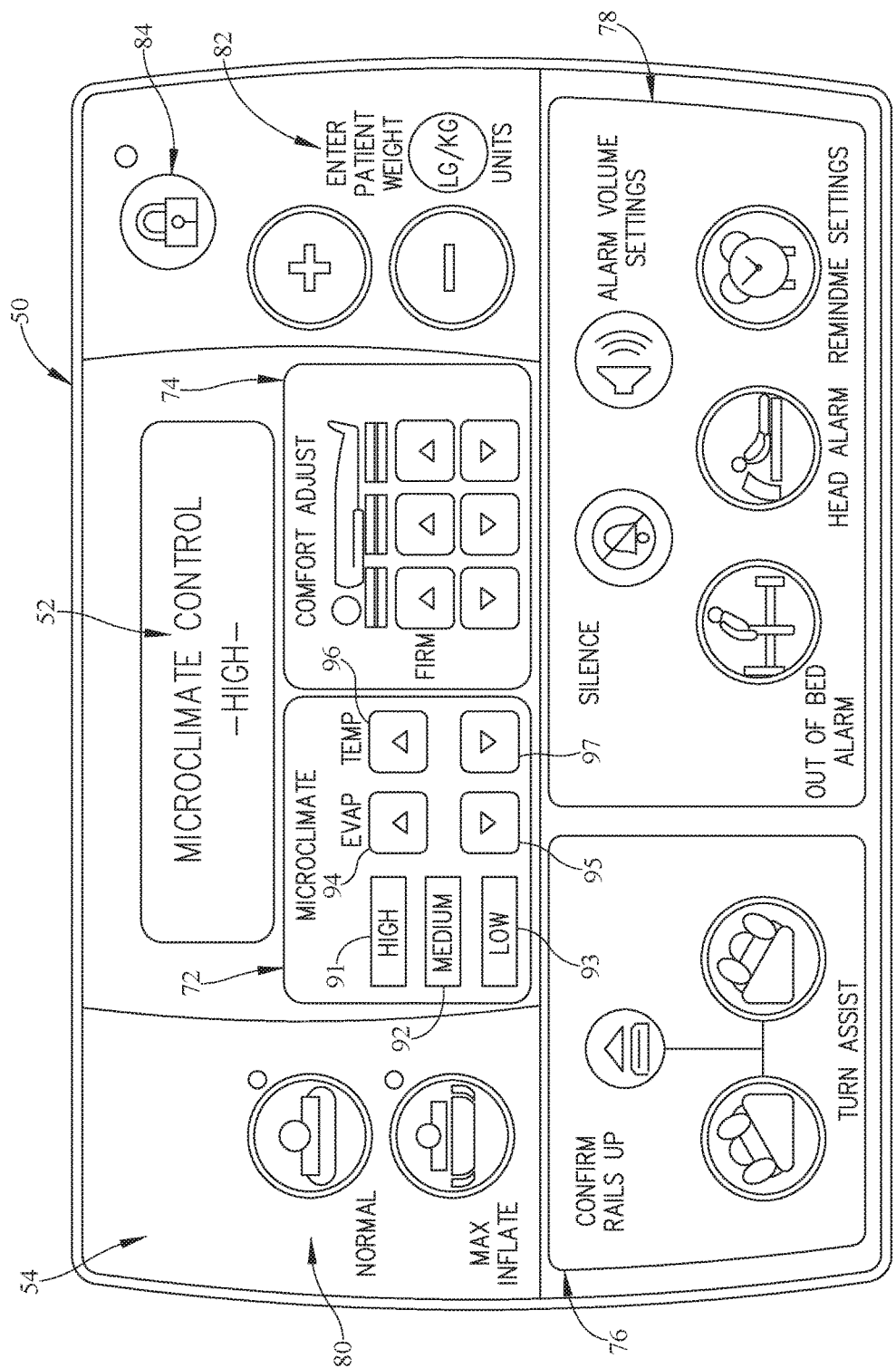
FIG. 4 is a detail view of an illustrative user interface included in the air box of FIGS. 1 and 2 and includes buttons configured to control air box settings.

The air box 18 includes an air handling unit 45, a housing 46, a connector hose 48, and a user interface 50 as shown in FIG. 2. The housing 46 holds an in-line sensor unit 34 and the air handling unit 45 as suggested in FIGS. 1 and 2. The connector hose 48 extends from the housing 46 to the support surface 16 to couple the air handling unit 45 to the support surface 16. The user interface 50 is coupled to the housing 46 and includes an LCD display 52 and a number of push buttons 54 as shown in FIG. 4. In other embodiments, the user interface 50 may be a touch screen or another suitable interface.

Figure 3:
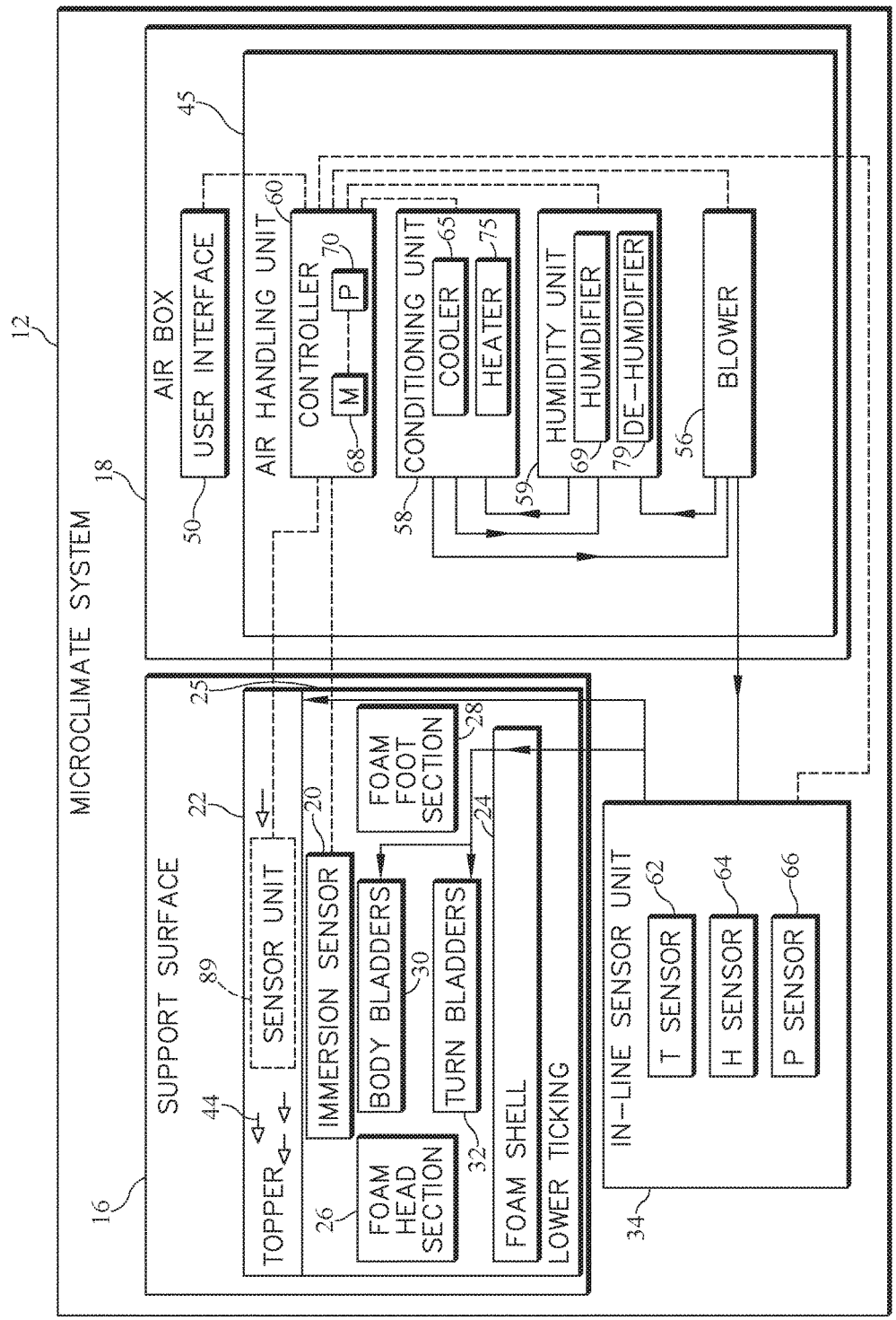
FIG. 3 is a diagrammatic view of the microclimate system of FIGS. 1 and 2, the air box includes an air handling unit with a controller, an air conditioner unit, a humidity unit, and a blower, and the controller is coupled to the immersion sensor and operable to vary one or more of a flow rate, temperature, and humidity of the air moved by the air handling unit if the controller and immersion sensor detect a compressed portion of the support surface degrading the performance of the microclimate system.

Referring now to FIG. 3, the air handling unit 45 is shown to include a blower 56, a conditioning unit 58, a humidity unit 59, the in-line sensor unit 34, and a controller 60. The blower 56 is coupled to the topper 22 (through the conditioning unit 58) and the bladders 30, 32 to provide air flow to the topper 22 and the bladders 30, 32. The conditioning unit 58 is coupled to the blower 56 and the topper 22 and is configured to condition air moved from the blower 56 to the topper 22. The humidity unit 59 is configured to control the humidity of the air moved from the blower 56 to the topper 22. The in-line sensor unit 34 is configured to detect information about the flow of air moved by the air box 18 so that operation of the microclimate system 12 can be adjusted to produce a flow of air with a desired temperature, humidity, and/or pressure. The blower 56, the conditioning unit 58, the humidity unit 59, and the in-line sensor unit 34 are electrically coupled to the controller 60 as shown in FIG. 3. The controller 60 is illustratively coupled to the user interface 50 to send and receive information to/from a user. Pneumatic connections are illustrated in FIG. 3 using solid lines with arrows suggesting the direction of flow and electrical connections are illustrated in FIG. 3 with dotted lines.

The conditioning unit 58 includes a cooler 65 and a heater 75 that are configured to cool or heat air sent from the blower 56 to the topper 22 as show in FIG. 3. In some embodiments, the conditioning unit 58 may be omitted or may include other combinations of a cooler, a heater, a humidifier, and/or a dehumidifier.

The humidity unit 59 includes a humidifier 69 and a dehumidifier 79 as shown in FIG. 3. The humidity unit 59 is electrically coupled to the controller 60 and fluidly coupled to the blower 56 and the conditioning unit 58 so that the humidity unit 59 may be selectively operated to add or remove moisture from air moved by the blower 56 to the topper 22. In some embodiments, the humidity unit 59 may be optionally coupled to the conditioning unit 58 to receive recirculated air from the conditioning unit 58. This recirculation loop may allow the air box 18 to further adjust humidity and/or temperature of air that is eventually passed on to the topper 22.

As one example, the humidifier 69 includes a fluid reservoir and misting element (not shown) for adding humidity to air moved through the topper 22. As another example, the dehumidifier 79 includes a cooling chamber and cooling element (not shown) for cooling air passing through the humidity unit 59 so that water vapor condenses and falls out of the air moved through the topper 22. In other embodiments, the dehumidifier 79 may include a desiccant-filled chamber (not shown) for absorbing humidity from air moved through the topper 22.

The in-line sensor unit 34 is configured to produce signals indicative of one or more of a temperature, a humidity, and a pressure of air moving to the topper 22. The controller 60 cooperates with the in-line sensor to adjust the properties of the airflow and control the performance of the microclimate system 12. The in-line sensor unit 34 is coupled between the air handling unit 45 and the topper 22 as shown in FIG. 3.

The in-line sensor unit 34 illustratively includes a temperature sensor 62, a humidity sensor 64, and a pressure sensor 66. In the illustrative embodiment, the in-line sensor unit 34 is enclosed in the housing (not shown) of the blower 56. However, in other embodiments, the in-line sensor unit 34 may be located in the connector hose (not shown) of the blower 56 or in an inlet (not shown) of the topper 22.

Each of the sensors 62, 64, 66 included in the in-line sensor unit 34 is configured to detect an input factor corresponding to the conditioned air provided to the topper 22 from the air box 18. Additionally, each of the sensors 62, 64, 66 is coupled to the controller 60 to communicate the signals indicative of the detected input factors to the controller 60. In other embodiments, the in-line sensor unit 34 may only include one or two of the sensors 62, 64, 66 or may include other types of sensors configured to detect environmental factors corresponding to the surroundings of the support surface 16 and the air box 18.

In other embodiments, them microclimate system 12 includes an environmental sensor unit 89 and the in-line sensor unit 34 unit may be omitted. The environmental sensor unit 89 may be housed in the housing 46 of the air box along an intake path of the blower 56. In other embodiments, the environmental sensor unit 89 may be located outside the housing 46 and/or spaced apart from the intake path of the blower 56. In some embodiments, the environmental sensor unit 89 may be positioned in the topper 22. The environmental sensor unit 89 may include a temperature sensor, a humidity sensor, and a pressure sensor. Each of the sensors included in the environmental sensor unit 89 is configured to detect an environmental factor corresponding to the surroundings of the support surface 16 and the air box 18. Each of the sensors is also coupled to the controller 60 to communicate the detected environmental factors to the controller 60.

The controller 60 is operable to receive user-input signals from the user interface 50 and control the flow of air moved to the topper 22 of the microclimate system 12 based on the user-input signals to achieve a desired performance of the microclimate system 12. In particular, the controller 60 is configured to adjust the operation of the air box 18 to provide a rated level of heat and moisture withdrawal through the top face 36 of the support surface 16 by adjusting the flow rate, temperature, and humidity of air from the air box 18 to the support surface 16. The controller 60 is configured to adjust operation of the air box 18 based on the user-input signals, environmental factors provided by the sensors 62, 64, 66, and/or the immersion signals provided by the immersion sensor 20. In operation, the controller 60 of the microclimate system 12 is configured to perform process 110 shown in FIG. 8.

When the airflow along the interface is not restricted due to compression of the topper 22, the controller 60 cooperates with the in-line sensor unit 34 to adjust the output of the air box 18 to maintain the rated performance selected with the user interface 50. The microclimate system 12 may underperform in compressed portions of the support surface 16, for example, due to restricted airflow through compressed portions of the top and middle layers 43, 42. The controller 60 is operable to modify one or more of the flow, temperature, and humidity of air moved to the support surface 16 based on the immersion signals received from the immersion sensor 20 so that the desired performance of the microclimate system 12, including the performance in the compressed portions, is achieved.

As shown in FIG. 3, the controller 60 illustratively includes a memory 68 configured to store information and instructions and a processor 70 coupled to the memory 68 to execute the instructions held in the memory 68. The controller 60 continuously or intermittently receives immersion signals from the immersion sensor 20 that are indicative of a measured immersion value of a patient supported on the microclimate system 12. The controller 60 compares the measured immersion value with reference values. In some embodiments, the reference values are stored in a reference table in the memory 68. The controller 60 controls the conditioning unit 58, the humidity unit 59, and the blower 56 to modify the flow of air in response to the comparison between the measured immersion value and the reference value to achieve the desired performance through the support surface 16 including compressed portions of the support surface 16.

Referring now to FIG. 4, the user interface 50 includes push buttons 54 adapted to provide user inputs to the controller 60. The push buttons 54 are organized to provide a microclimate control panel 72, a comfort control panel 74, a turn-assist control panel 76, an alarm panel 78, an inflation control panel 80, a weight entry panel 82, and a user interface lock button 84 as shown in FIG. 4. Each panel 72, 74, 76, 78, 80 is configured to control a different aspect of the microclimate system 12.

The microclimate control panel 72 is configured to allow a user to automatically or manually control the microclimate system 12. Specifically, a user may select an automatic (or predetermined) level of microclimate control desired from the microclimate system 12 by pressing a high, medium, or low button 91, 92, 93. Alternatively, a user may select custom levels of moisture removal and interface temperature by pressing up and down arrows 94, 95, 96, and 97.

In the illustrative embodiment, the performance of the microclimate system 12 is measured in total heat withdrawal (W/m$^2$) and/or evaporative capacity (g/m$^2$-hr). In other embodiments, performance may also be measured in dry heat withdrawal (W/m$^2$). In order to ensure that the preset levels of microclimate system 12 performance are met when an automatic level is selected, the controller 60 of the exemplary microclimate system 12 considers immersions signals received from the immersion sensor 20 and, sometimes, environmental factors received from the in-line sensor unit 34 when setting operating parameters for the blower 56, the conditioning unit 58, and the humidity unit 59.

For example, the high setting of the microclimate system 12 may be rated for performance of about 85 W/m$^2$ total heat withdraw and greater than 10 g/m$^2$-hr evaporative capacity. Under normal operating parameters, such performance by the microclimate system 12 may be achieved using default operating parameters in a room at about 70 degrees F. and about 50 percent humidity.

However, with the blower 56, conditioning unit 58, and humidity unit 59 operating under the same normal operating parameters, performance may be degraded in compressed portions of the support surface 16 such that not enough heat withdrawal or evaporation is provided causing a patient to become wet from sweat or body fluids. In order to maintain the rated performance in compressed portions of the topper 22, the exemplary microclimate system 12 is configured to consider an immersion factor as measured by the immersion sensor 20 when controlling operating parameters for the blower 56, the conditioning unit 58, and the humidity unit 59.

Figure 5:
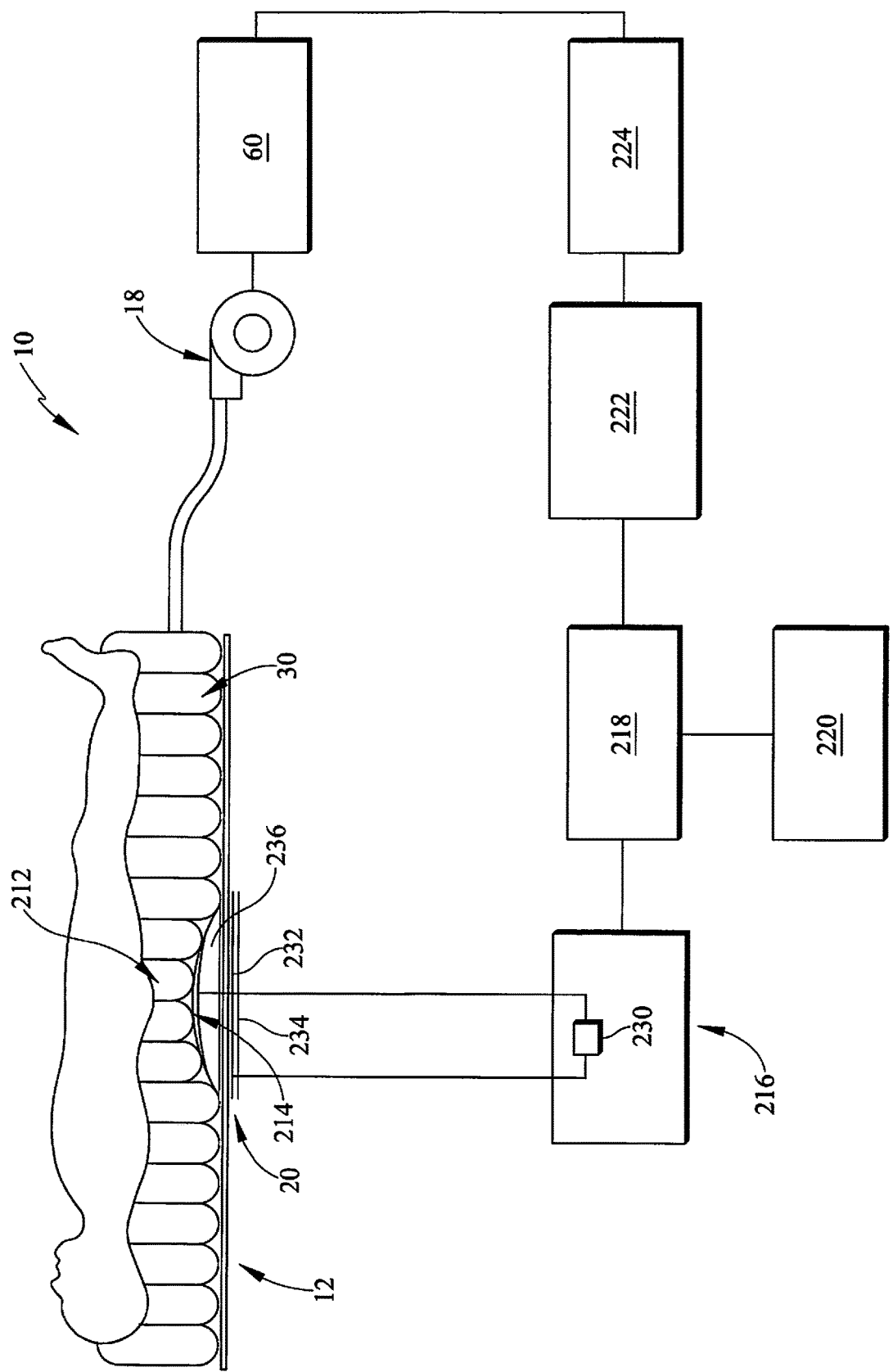
FIG. 5 is a diagrammatic view of the microclimate system of FIGS. 1 and 2, the immersion sensor is located under a sacral region of the patient, and the illustrative immersion sensor comprises an inductive sensor including a metal element and an inductive element.

The immersion sensor 20 is configured to produce signals indicative of the immersion of the patient into the support surface 16 as shown in FIG. 5. The immersion of the patient into the support surface 16 may be used to determine if any portion of the topper 22 is compressed and/or experiencing high pressure and degrading the rated performance of the microclimate system 12. The controller 60 receives the immersion signals from the immersion sensor 20 and controls the operating parameters for the blower 56, the conditioning unit 58, and the humidity unit 59 based on the immersion signals. As a result, the performance of the microclimate system 12 is maintained in compressed portions of the topper 22.

Immersion of the patient into the support surface 16 may compress areas of the topper 22 such as, for example, portions of the middle layer 42 and the top layer 43. Tissue breakdown is more likely to occur in areas where the topper 22 is compressed and performance is degraded. Typically, compression of the support surface 16 is due to high local pressures caused by, for example, relatively heavy patients, elevation of the head of the bed 10, and prominent protruding bone structure in patients.

In the illustrative embodiment, the immersion sensor 20 comprises an inductance sensor 20. In other embodiments, the immersion sensor 20 comprises a pressure sensor, a delta-pressure sensor, a capacitive sensor, or any other suitable device. In some embodiments, the immersion sensors 20 that comprise pressure sensors correlate increased pressures with increased immersion of the patient into the support surface 16. The immersion sensors 20 may measure the pressure of the bladders such as, for example, the body bladders 30.

The illustrative immersion sensor 20 measures the immersion of the patient resulting from deformation of the topper 22. In the illustrative embodiment, the immersion sensor 20 includes a metal element 212 and at least one inductive element 214 as shown in FIG. 5. The metal element 212 and the inductive element 214 cooperate to form a position detector configured to detect movement and deformation caused by immersion of the patient into the support surface 16.

The metal element 212 is illustratively in the form of a flexible film of a thin metallic foil. The metal element 212 is movable and deformable in space by being coupled to the bottom layer 41 of the topper 22. As an example, the metal element 212 is between about 10 μm and about 40 μm thick. The metal element 212 is spaced apart from the inductive element 214 to form a gap therebetween.

The inductive element 214 comprises an induction coil, as an example. The inductive element 214 is spaced apart from and positioned below the metal element 212. In the illustrative embodiment, the inductive element 214 is coupled to a bottom surface of the body bladders 30 as shown in FIGS. 2 and 5. In some embodiments, the inductive element 214 is supported on a reinforcing member 236. The reinforcing member 236 is positioned near the region of the element being supported which has the largest mass or which is protuberant. As shown in FIG. 5, the inductive element 214 is illustratively located below a sacral region of the patient. In other embodiments, the immersion sensor 20 is located in alternate locations in the support surface 16. In yet other embodiments, the immersion sensor 20 is located outside of the support surface 16.

The inductive element 214 is illustratively an impedance-varying element operable to measure the position of the closest point of the supported element, such as the patient. The impedance-varying element may include one or more of a resistive element, e.g. a conducive foam; a capacitive element, e.g. in which a flexible film of a thin metal foil which may be constituted by the flexible film of metal foil 212 is one of the components of the capacitor; an inductive element, in particular a measurement induction coil; and an element made up of any combination of the mentioned elements.

The illustrative immersion sensor 20 further includes a measurement bridge 230, an oscillator device 216, an amplifier device 218, a reference setting device 220, a proportional-plus-integral regulator device 222, and a matching device 224. The oscillator 216 is coupled to the inductive element 214 such as an inductive coil. A gain of the amplifier device 218 may be adjusted by the reference setting device 220. The amplifier 218 is coupled to the proportional-plus-integral regulator device 222 coupled to a matching device 224 whose output is coupled to the controller 60.

Figure 6:
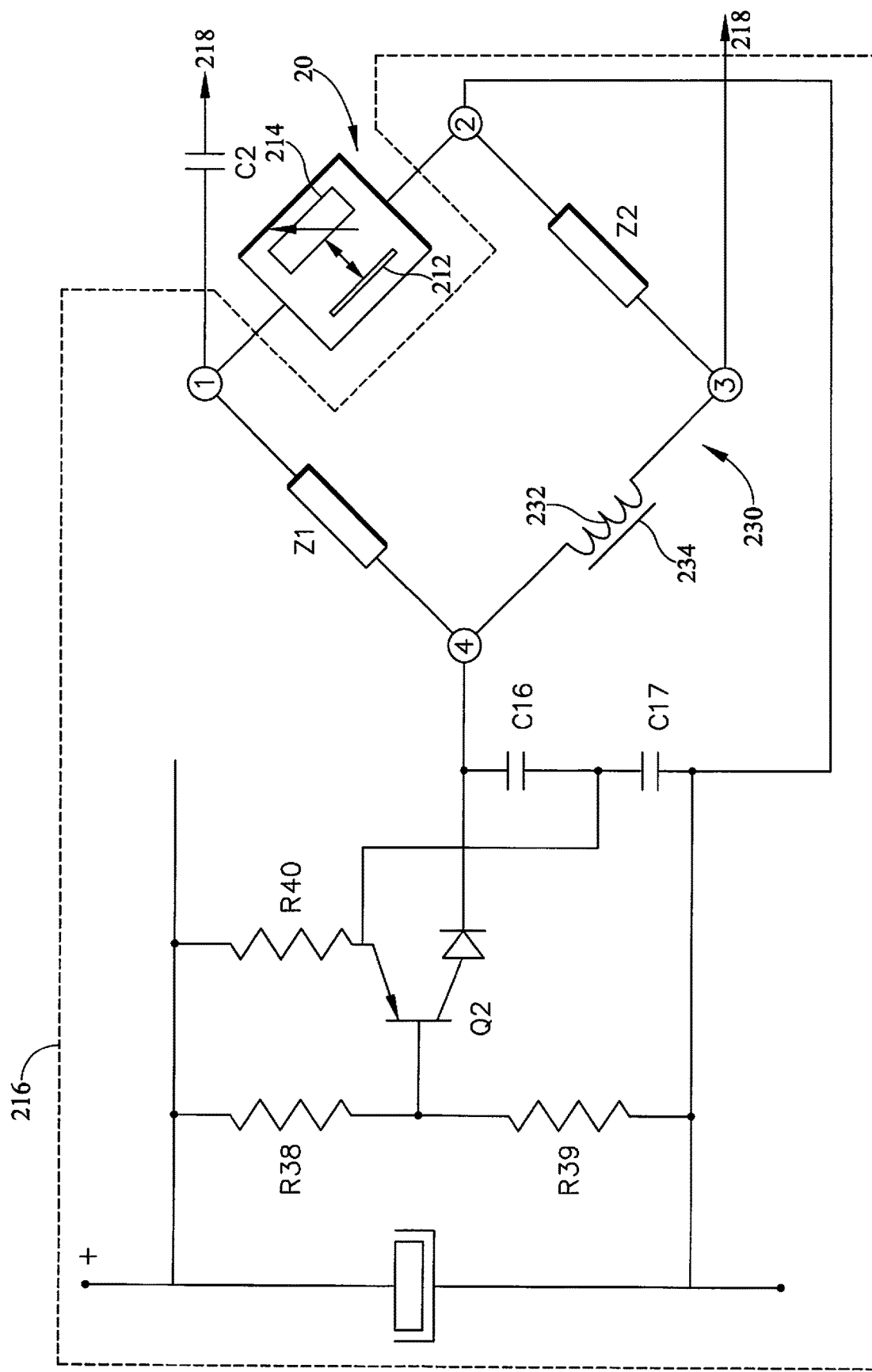
FIG. 6 is an oscillator electronic circuit portion of the immersion sensor that integrates movement and deformation of the support surface in a measurement electronic bridge.

The measurement bridge 230 includes a number of resistors R38, R39, R40, capacitors, C2, C16, C17, induction coil 232, and other components arranged as shown in FIG. 6. The measurement bridge 230 cooperates with the other components of the immersion sensor 20 to detect an immersion of the patient into the support surface 16 and to produce immersion signals indicative of the immersion.

The vertices of the branches of the measurement bridge 230 are respectively referenced 1, 2, 3, and 4. For example, the inductive element 214 may be connected to the vertices 1 and 2. The vertex 1 is connected to the vertex 4 via a branch including a first impedance Z1, the vertex 4 is connected to the vertex 3 via a branch which is situated opposite from the branch including the inductive element 214. In this example, this opposite branch preferably includes a shielding induction coil 232. The vertex 3 is connected to the vertex 2 via a branch including a second impedance Z2 in this example. The vertices 1 and 3 of the measurement bridge are also connected to the amplifier 218, optionally via at least one decoupling capacitor C2.

The oscillator 216 may include a static portion constituted by the measurement bridge 230, capacitors C16 and C17, and a dynamic portion constituted by the transistor Q2 and its bias elements. The dynamic portion is connected to the vertices 4 and 2 of the measurement bridge 230.

According to the present disclosure, when the impedance-varying element 214 is an inductive element in particular constituted by a measurement induction coil, as shown in FIG. 6, the shielding induction coil 232 may be identical to the measurement induction coil 214 so that, when they are subjected to outside influences, e.g. caused by metal elements such as the bed, the shielding induction coil 232 and the measurement induction coil 214 vary identically. Similarly, the two other branches preferably have identical impedances Z1, Z2.

To render the opposite branches of the measurement bridge 230 as identical as possible, it is preferable to combine the shielding induction coil 232 with a second piece of metal foil 234 identical to the moving flexible film of thin metal foil 212, the second piece of metal foil 234 being arranged at a predetermined distance from the shielding induction coil 232. By means of this design of the measurement bridge 230, it is possible to set the bridge 230 to a zero value for a predetermined distance value, e.g. in the vicinity of zero, i.e. when the moving flexible film of thin metal foil 212 almost touches the induction coil 214.

Figure 7:
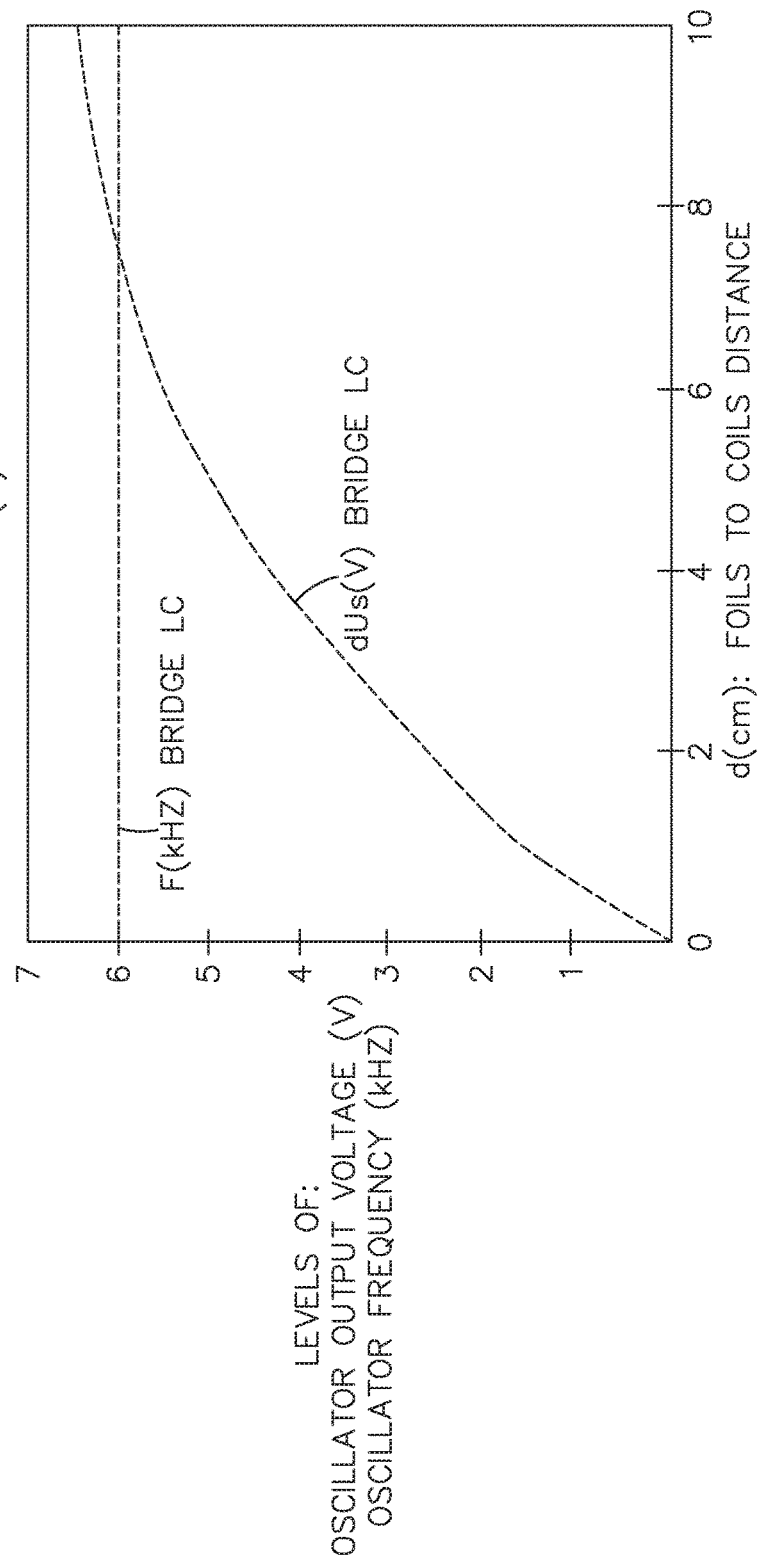
FIG. 7 is a frequency and voltage curve obtained using the electronic bridge of FIG. 6.

FIG. 7 shows, in dashed lines, the curves giving frequency and voltage as a function of the distance between the closest point of the deformed metal foil 212 and the measurement induction coil 214 obtained with the immersion sensor 20. It can be observed that the frequency is generally constant so that the oscillator 216 has become an oscillator whose frequency is fixed under the operation conditions provided, in this example at about 6 kHz. The voltage curve varies considerably as a function of position, from a zero value for a distance initially set at zero to a voltage of about 6.5 volts for a distance of 10 cm, which represents a difference of 6.5 volts. The voltage curve is substantially proportional over a major portion of the distance, which portion is the portion in which the regulation may take place.

Figure 8:
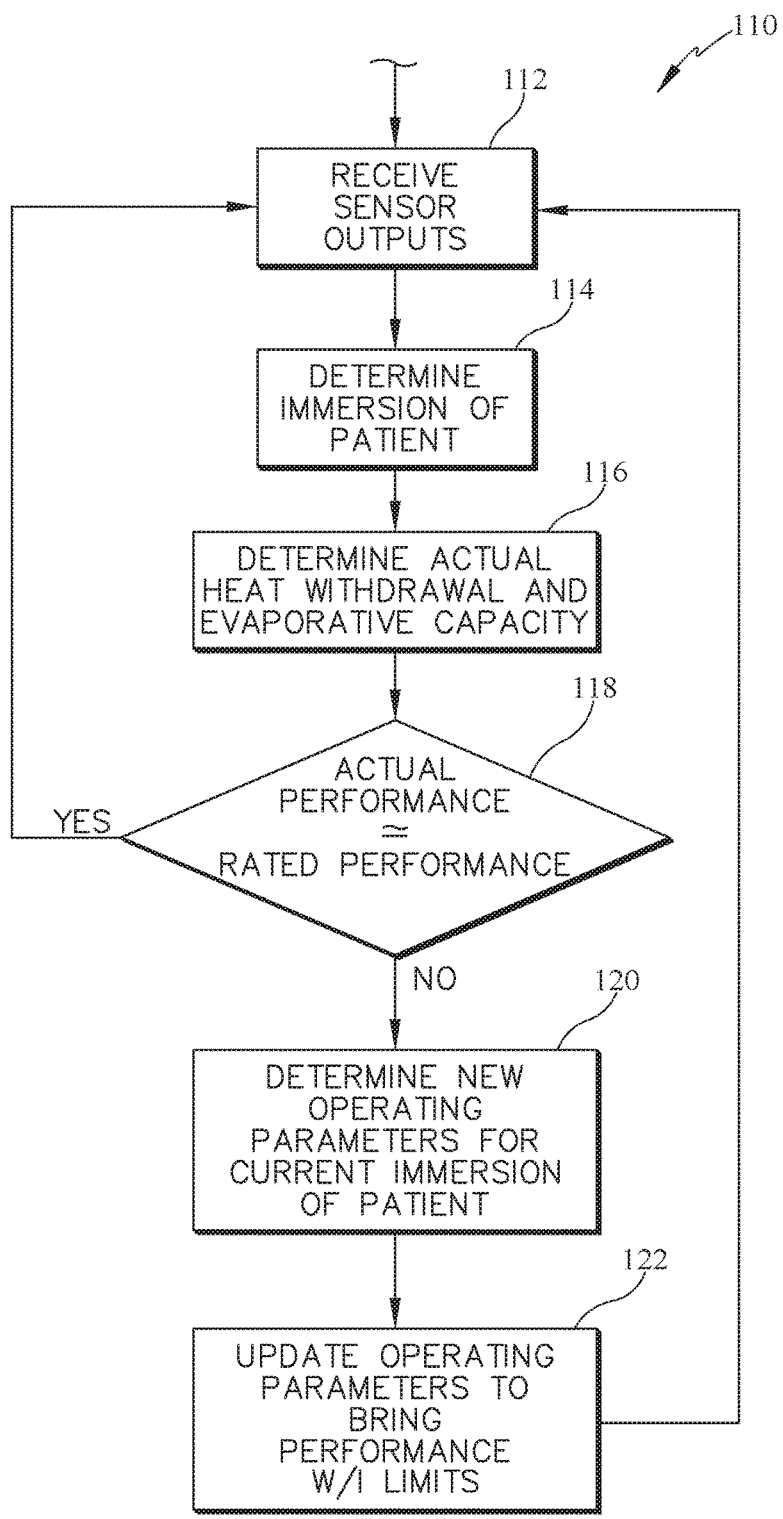
FIG. 8 is a flow chart of a process performed by the controller of the microclimate system to account for immersion of the patient during operation of the microclimate system in order to deliver rated performance when portions of the support surface are compressed and degrading performance.

Referring now to FIG. 8, an illustrative process 110 for controlling the microclimate system is shown. The process 110 is illustratively performed by the controller 60 of the microclimate system 12. The process 110 includes a step 112 in which the controller 60 receives sensor outputs from the immersion sensor 20, the in-line sensor unit 34, and the user interface 50. The illustrative controller 60 receives a temperature input from the temperature sensor 62, a humidity input from the humidity sensor 64, and a pressure input from the pressure sensor 66 in step 112.

After receiving the sensor outputs, the process 110 advances to a step 114 in which the controller 60 determines the immersion of the patient into the support surface 16. In the illustrative embodiment, the immersion is determined by looking up an immersion value from an immersion look-up table stored in the memory 68 based on the immersion signal received by the controller 60.

Next, the process 110 advances to a step 116 in which the controller 60 determines an actual heat withdrawal and evaporative capacity performance level for the microclimate system 12. In the illustrative embodiment, the actual performance levels are determined by looking up actual performance levels from a system-specific performance look-up table. The actual heat withdrawal and evaporative capacity performance levels are looked up based on environmental factors (temperature, humidity, pressure, etc.), on current operating parameters of the air box 18 (blower speeds and conditioning unit settings corresponding to various levels of microclimate control), and on the immersion value determined in step 114. The system-specific performance look-up table is populated by empirical testing of a specific support surface 16 and air box 18 combination. In other embodiments, the system-specific performance look-up table may be populated by mathematical analysis of a specific support surface 16 and air box 18 combination.

In some embodiments, the controller 60 may determine the actual heat withdrawal and evaporative capacity performance level for the microclimate system 12 by plugging values corresponding to immersion values into system-specific performance equations. The system-specific performance equations may be developed by empirical testing and/or mathematical analysis of a specific support surface 16 and air box 18 combination.

Next, the process 110 performs a decisions step 118 in which the determined actual performance levels are compared to rated performance levels for the microclimate system 12. If the actual performance levels are equal to or within an acceptable range around the rated performance levels, the process 110 loops back to step 112 and re-checks the sensor outputs. If the actual performance levels do not meet the rated performance levels, then the process 110 proceeds to a step 120.

In step 120, the process 110 determines new operating parameters for the air box 18 (blower speeds, conditioning unit settings, and humidity unit settings corresponding to various levels of microclimate control) that will deliver the rated performance levels under current conditions. In the illustrative embodiment, the new operating parameters are determined by looking up operating parameters from a system-specific parameter look-up table. The new operating parameters are looked up based on the immersion value and environmental factors (temperature, humidity, pressure). The system-specific parameter look-up table is populated by empirical testing of a specific support surface 16 and air box 18 combination. In other embodiments, the system-specific parameter look-up table may be populated by mathematical analysis of a specific support surface 16 and air box 18 combination.

In some embodiments, the controller 60 may determine the new parameters for the microclimate system 12 by plugging values corresponding to immersion values into a set of system-specific parameter equations. The system-specific parameter equations may be developed by empirical testing and/or mathematical analysis of a specific support surface 16 and air box 18 combination.

After the new operating parameters are determined in step 120, the controller 60 proceeds to step 122 in which the current operating parameters of the air box 18 are updated to the new operating parameters determined in step 120. When the updated operating parameters are in place, the process 110 loops back to step 112 and rechecks the sensor outputs. Thus, the operating parameters of the air box 18 (blower speed, conditioning unit operation, and humidity unit operation) continue to be adjusted based on the immersion of the patient into the support surface 16 detected by the immersion sensor 20 so that the microclimate system 12 is adapted to provide rated performance levels of heat withdrawal and evaporative capacity when portions of the support surface 16 experience high pressure and airflow is restricted.

Although certain illustrative embodiments have been described in detail above, variations and modifications exist within the scope and spirit of this disclosure as described and as defined in the following claims.

The invention claimed is:

1. A microclimate system comprising
a support surface including a topper, the topper configured to conduct air along a top face of the support surface so that heat and moisture from a patient lying on the support surface are drawn away from the top face of the support surface,
an air box including a controller and a blower coupled to the controller and coupled to the topper, and
an immersion sensor unit coupled to the controller, the immersion sensor unit detecting the immersion of the patient into the support surface,
wherein the controller includes a processor and a memory device, wherein the memory device includes instructions that, when executed by the processor, operates the controller such that the controller receives the immersion information from the immersion sensor unit, determines if current operating parameters of the air box provide a rated level of heat withdrawal or evaporative capacity through the topper based at least in part on the amount of immersion of the patient into the support surface, modifies the current operating parameters of the air box to compensate for restriction of the air flow in the topper if the current operating parameters of the air box do not provide the desired level of performance by the topper and the immersion information indicates that the immersion of the patient into the support surface restricts the flow of air in the topper.

2. The microclimate system of claim 1, wherein the desired level of performance includes a minimum level of heat withdrawal.

3. The microclimate system of claim 2, wherein the desired level of performance includes a minimum level of evaporative capacity.

4. The microclimate system of claim 3, wherein the controller modifies the flow rate of the air delivered to the support surface by the air box.

5. The microclimate system of claim 4, wherein the controller modifies the humidity of the air delivered to the support surface by the air box.

6. The microclimate system of claim 5, wherein the controller modifies the temperature of the air delivered to the support surface by the air box.

7. The microclimate system of claim 1, wherein the controller modifies the humidity of the air delivered to the support surface by the air box.

8. The microclimate system of claim 1, wherein the immersion sensor comprises an induction sensor including a metal element and an inductive element.

9. The microclimate system of claim 8, wherein the inductive element includes an inductive coil spaced apart from and positioned beneath the topper, the metal element includes a metal foil positioned between the topper and the inductive coil, and the metal foil is spaced apart from the inductive coil to form a gap therebetween.

10. The microclimate system of claim 9, wherein the immersion sensor further includes a measurement bridge, an oscillator device, an amplifier device, a reference setting device, a proportional-plus-integral regulator device, and a matching device, wherein the oscillator device is coupled to the inductive element, and wherein a gain of the amplifier device is adjusted by the reference setting device.

11. A microclimate system comprising
a topper,
an air box including a controller and a blower coupled to the controller and coupled to the topper, and
an immersion sensor unit coupled to the controller, the immersion sensor unit detecting an immersion of a patient into the topper,
wherein the controller includes a processor and a memory device, wherein the memory device includes instructions that, when executed by the processor, operates the controller such that the controller receives the immersion information from the immersion sensor unit, determines if current operating parameters of the air box provide a rated level of heat withdrawal or evaporative capacity through the topper based at least in part on the amount of immersion of the patient into the topper, and modifies the current operating parameters of the air box to compensate for restriction of the air flow in the topper if the current operating parameters of the air box do not provide the rated level of heat withdrawal or evaporative capacity through the topper and the immersion sensor indicates that the amount of immersion of the patient into the support surface restricts the flow of air in the topper.

12. The microclimate system of claim 11, wherein the controller modifies a flow rate of the air delivered to the topper by the air box.

13. The microclimate system of claim 11, wherein the controller modifies a humidity of the air delivered to the topper by the air box.

14. The microclimate system of claim 11, wherein the controller modifies a temperature of the air delivered to the topper by the air box.

15. The microclimate system of claim 11, wherein the immersion sensor comprises an induction sensor including a metal element and an inductive element.

16. A method for controlling a microclimate system including a topper and an air box coupled to the topper to move pressurized air to the topper, the method comprising, detecting, using an immersion sensor, the immersion of a patient supported on the microclimate system into the topper, determining if current operating parameters of the air box provide a rated level of heat withdrawal or evaporative capacity through the topper, based at least in part on the immersion detected by the immersion sensor, and updating the current operating parameters of the air box to compensate for restriction of the air flow in the topper if the current operating parameters of the air box do not provide the rated level of heat withdrawal or evaporative capacity through the topper and the immersion sensor indicates that the amount of immersion of the patient into the support surface restricts the flow of air in the topper.

17. The method of claim 16, wherein determining if the current operating parameters of the air box will provide the rated level of heat withdrawal or evaporative capacity includes (i) looking up an actual level of heat withdrawal or evaporative capacity corresponding to the received information in a first look-up table and (ii) comparing the actual level of heat withdrawal or evaporative capacity parameters with the rated level of heat withdrawal and evaporative capacity.

18. The method of claim 16, wherein updating the current operating parameters includes modifying one or more of a flow rate, temperature, and humidity of pressurized air moved by the air box to the topper.

19. The method of claim 16, wherein the immersion sensor comprises an inductive sensor.

20. The method of claim 16, wherein the immersion sensor comprises a pressure sensor.

* * * * *